(12) United States Patent
Ichikawa (10) Patent No.: US 6,460,400 B1
(45) Date of Patent: Oct. 8, 2002

(54) EXHAUST GAS MEASURING INSTRUMENT

(75) Inventor: Jun Ichikawa, Hino (JP)

(73) Assignee: Hino Jidosha Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/269,240

(22) PCT Filed: Sep. 18, 1997

(86) PCT No.: PCT/JP97/03289
§ 371 (c)(1),
(2), (4) Date: Mar. 22, 1999

(87) PCT Pub. No.: WO98/13680
PCT Pub. Date: Apr. 2, 1998

(30) Foreign Application Priority Data

Sep. 27, 1996 (JP) .............................................. 8-277111

(51) Int. Cl.[7] ................................................. G01N 7/00
(52) U.S. Cl. ...................................... 73/23.31; 73/118.1
(58) Field of Search ............................. 73/23.31, 23.33, 73/863.03, 116, 117.3, 863.01, 204, 863.11, 863.51, 863.55, 864.34, 864.81, 118.1

(56) References Cited

U.S. PATENT DOCUMENTS

| 4,361,028 A | * | 11/1982 | Kamiya et al. | ............ | 73/23.33 |
| 5,187,972 A | * | 2/1993 | DeFriez | ...................... | 73/23.2 |
| 5,456,124 A | * | 10/1995 | Colvin | ..................... | 73/863.11 |
| 5,596,154 A | * | 1/1997 | Baughman | ............... | 73/863.01 |
| 5,821,435 A | * | 10/1998 | Kojima | ..................... | 73/863.01 |

FOREIGN PATENT DOCUMENTS

| JP | 8-254487 | 10/1996 |
| JP | 9-145562 | 6/1997 |
| WO | WO98/13680 | 4/1998 |

OTHER PUBLICATIONS

International Search Report Dec. 24, 1997.

* cited by examiner

*Primary Examiner*—Eric S. McCall
(74) *Attorney, Agent, or Firm*—McCormick, Paulding & Huber LLP (57) ABSTRACT

An exhaust gas measuring instrument has a mini-dilution tunnel (22) in which a part of exhaust in the exhaust pipe (15) of an engine is introduced through sampling tube (30) and diluted with air. The exhaust gas is diluted in the mini-dilution tunnel (22), a high response differential pressure type extracted gas flow meter (31 and 40) measures the exhaust gas flow rate (Qs) in the sampling tube (30). A high response differential pressure type bypassed gas flow meter (29 and 39) measures the exhaust gas flow rate (Qb) in the exhaust pipe (15). The flow rate split ratio R=Qb/Qs is obtained by dividing the exhaust gas flow rate (Qb) by the exhaust gas flow rate (Qs). A calibration coefficient (k) of the flow rate split ratio is obtained and the calibrated flow rate split ratio (k.R) is calculated by multiplying the flow rate split ration by the calibration coefficient.

11 Claims, 4 Drawing Sheets

EXHAUST GAS MEASURING INSTRUMENT

TECHNICAL FIELD

The present invention relates to an exhaust gas measuring instrument using a mini-dilution tunnel to measure the amount of emission of various components in exhaust gas from an engine. The mini-dilution tunnel is arranged such that a part of exhaust gas is extracted from an exhaust pipe of the engine and introduced into the mini-dilution tunnel through a sampling tube and then diluted with air to lower the exhaust gas temperature.

BACKGROUND ART

A mini-dilution tunnel is used to measure the amount of emission of various components in exhaust gas from engines, particularly diesel engines. The mini-dilution tunnel lowers the temperature of extracted exhaust gas to 52° C., for example, thereby creating a condition in which various components in the exhaust gas condense into particulate matter as a result of the lowering in temperature. An exhaust gas measuring instrument using a mini-dilution tunnel measures the concentration of exhaust gas components such as nitrogen oxides in a state approximately similar to that in a case where the exhaust gas is released into the atmosphere, and obtains the amount of emission of the exhaust gas components.

In an exhaust gas measuring method using a mini-dilution tunnel, the amount (weight) of emission of various components in exhaust gas from an engine is obtained in the form of the product of the concentration of various exhaust gas components obtained by analyzing the exhaust gas diluted in the mini-dilution tunnel, the flow rate of the diluted exhaust gas passing through the mini-dilution tunnel, the diluting ratio in the mini-dilution tunnel, and the flow rate split ratio, which is the ratio of the flow rate of exhaust gas passing through an exhaust pipe to the flow rate of exhaust gas introduced into a sampling tube.

It is essential to measure the amount of emission of various components in exhaust gas from an engine in each output or operation mode or the like accurately and with a minimal delay in time for the evaluation of the performance of the engine operated in various operation modes and for the judgment of the conformability to the emission regulations. An exhaust gas measuring instrument using a mini-dilution tunnel need not dilute the whole quantity of exhaust gas and is therefore capable of measuring the amount of emission of various components in exhaust gas by using a small-sized mini-dilution tunnel. Accordingly, the whole exhaust gas measuring instrument can be constructed in a compact structure.

However, the conventional exhaust gas measuring instrument using a mini-dilution tunnel was developed for the steady state operation mode of an engine, and it has a structure for measuring the concentration of exhaust gas components in the steady state. Because a long time is needed for the concentration to reach a stable state, the conventional exhaust gas measuring instrument cannot be used in the transient operation mode. In other words, the conventional exhaust gas measuring instrument using a mini-dilution tunnel cannot perform measurement of exhaust gas components in the transient operation mode because about 10 seconds is needed at 90% of response to a step input owing to the residence of exhaust gas in the sample tube and the delay in response of the detector.

DISCLOSURE OF INVENTION

An object of the present invention is to eliminate the disadvantages of the conventional exhaust gas measuring instrument and to provide a fast-response exhaust gas measuring instrument using a mini-dilution tunnel and capable of measuring the amount of various components in exhaust gas in the transient operation mode of an engine. A particular object of the present invention is to provide an exhaust gas measuring instrument in which a bypassed gas flow meter for measuring the exhaust gas flow rate in an exhaust pipe and an extracted gas flow meter for measuring the exhaust gas flow rate in a sampling tube are high response differential pressure type flow meters, respectively, so that it is possible to obtain a flow rate split ratio, which is the ratio of the exhaust gas flow rate in the exhaust pipe to the exhaust gas flow rate in the sampling tube in both the steady state and transient operation modes of the engine.

Another object of the present invention is to enable an even more accurate calibrated flow rate split ratio to be calculated in the exhaust gas measuring instrument using a mini-dilution tunnel by multiplying the flow rate split ratio obtained in the transient operation mode of the engine by a calibration coefficient. Other objects and advantages of the present invention will be made apparent in embodiments of the present invention, claims and drawings.

An exhaust gas measuring instrument according to the present invention has a mini-dilution tunnel in which a part of exhaust gas in an exhaust pipe of an engine is introduced through a sampling tube and diluted with air; a measuring means for measuring a specific component in the exhaust gas diluted in the mini-dilution tunnel; a high response differential pressure type extracted gas flow meter which measures the exhaust gas flow rate $Qs$ in the sampling tube; a high response differential pressure type bypassed gas flow meter which measures the exhaust gas flow rate $Qb$ in the exhaust pipe; and an arithmetic means for obtaining a flow rate split ratio $R=Qb/Qs$ by dividing the exhaust gas flow rate in the exhaust pipe, which is obtained by the high response differential pressure type bypassed gas flow meter, by the exhaust gas flow rate in the sampling tube, which is obtained by the high response differential pressure type extracted gas flow meter.

The exhaust gas measuring instrument according to the present invention further has a means for obtaining a calibration coefficient $k$ of the flow rate split ratio, and a means for obtaining a calibrated flow rate split ratio $k \cdot R$ by multiplying the flow rate split ratio by the calibration coefficient. The means for obtaining the calibration coefficient $k$ has a measuring means for measuring the concentration $Db$ of a specific substance in the exhaust gas in the exhaust pipe during a transient operation of the engine; a means for obtaining the whole quantity $Qb \cdot Db$ of the specific substance in the exhaust pipe by multiplying the exhaust gas flow rate $Qb$ in the exhaust pipe by the concentration of the specific substance in the exhaust gas in the exhaust pipe; a means for measuring the diluted exhaust gas flow rate $Qt$ in the mini-dilution tunnel; a measuring means for measuring the concentration $Dt$ of the specific substance in the exhaust gas diluted in the mini-dilution tunnel; a means for obtaining the whole quantity $Qt \cdot Dt$ of the specific substance in the mini-dilution tunnel by multiplying the diluted exhaust gas flow rate in the mini-dilution tunnel by the concentration of the specific substance in the exhaust gas diluted in the mini-dilution tunnel; and a means for calculating the concentration split ratio $Rc=(Qb \cdot Db)/(Qt \cdot Dt)$ by dividing the whole quantity of the specific substance in the exhaust pipe by the whole quantity of the specific substance in the mini-dilution tunnel. The calibration coefficient $k$ is obtained by dividing the concentration split ratio $Rc$ by the flow rate split ratio $R$.

The measuring instrument according to the present invention preferably has the following arrangements.

(1) The specific substance is nitrogen oxides.

(2) The high response differential pressure type extracted gas flow meter has a sample orifice installed in the sampling tube and obtains the exhaust gas flow rate Qs in the sampling tube on the basis of a pressure difference between two sides of the sample orifice produced by the exhaust gas passing through the sample orifice.

(3) The high response differential pressure type extracted gas flow meter has first and second pressure-receiving pistons and a transducer placed between the two pressure-receiving pistons to convert a pressure into an electric signal. The pressure on one side of the sample orifice and the pressure on the other side of the sample orifice are applied to the first and second pressure-receiving pistons, respectively, whereby a pressure difference at the sample orifice is converted into an electric signal.

(4) The high response differential pressure type extracted gas flow meter has first and second bellows and a resistant-wire strain gauge which converts deformation of a plate spring, which is placed between the two bellows, into an electric signal. The pressure on one side of the sample orifice and the pressure on the other side of the sample orifice are applied to the first and second bellows, respectively, whereby a pressure difference at the sample orifice is converted into an electric signal.

(5) The high response differential pressure type bypassed gas flow meter has a bypass orifice installed in the exhaust pipe and obtains the exhaust gas flow rate Qb in the exhaust pipe on the basis of a pressure difference between two sides of the bypass orifice produced by the exhaust gas passing through the bypass orifice.

(6) The high response differential pressure type bypassed gas flow meter has first and second pressure-receiving pistons and a transducer placed between the two pressure-receiving pistons to convert a pressure into an electric signal. The pressure on one side of the bypass orifice and the pressure on the other side of the bypass orifice are applied to the first and second pressure-receiving pistons, respectively, whereby a pressure difference at the by pass orifice is converted into an electric signal.

(7) The high response differential pressure type bypassed gas flow meter has first and second bellows and a resistant-wire strain gauge which converts deformation of a plate spring, which is placed between the two bellows, into an electric signal. The pressure on one side of the bypass orifice and the pressure on the other side of the bypass orifice are applied to the first and second bellows, respectively, whereby a pressure difference at the bypass orifice is converted into an electric signal.

(8) The bypassed gas flow meter measures the exhaust gas flow rate Qb in the exhaust pipe as the sum of the intake air quantity and the fuel flow rate.

(9) The bypassed gas flow meter, which measures the exhaust gas flow rate in the exhaust pipe, measures the flow rate of exhaust gas remaining after a part of exhaust gas has been extracted through the sampling tube.

(10) The mini-dilution tunnel has an air pump which supplies air into the mini-dilution tunnel, and a blower which discharges the exhaust gas diluted in the mini-dilution tunnel.

(11) The blower is rotated at a constant speed, and the number of revolutions of the air pump is controlled, whereby the flow rate split ratio R is feedback-controlled.

EMBODIMENTS OF THE INVENTION

Figure 1:
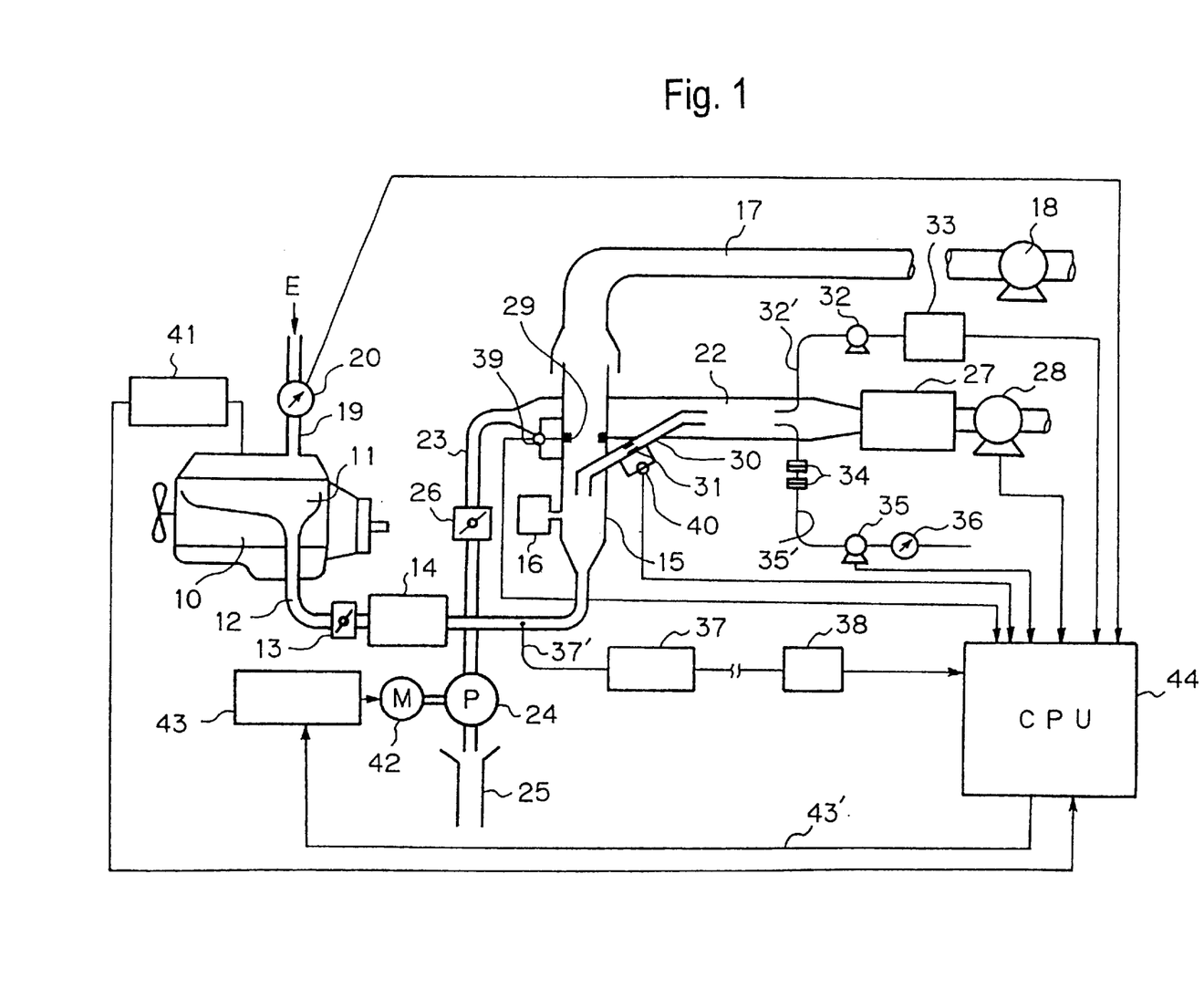
FIG. 1 is a layout plan showing the whole arrangement of an exhaust gas measuring instrument according to the present invention.

A plurality of embodiments of the present invention will be described below with reference to the drawings. However, the technical scope of the present invention is not limited to these embodiments but defined by the scope of the appended claims. FIG. 1 is a layout plan showing the whole arrangement of an exhaust gas measuring instrument according to one embodiment of the present invention. An exhaust pipe 12 is connected to an exhaust manifold 11 attached to a side of a diesel engine 10. A butterfly valve 13 for exhaust pressure regulation and a muffler 14 are connected to the exhaust pipe 12.

The outlet side of the muffler 14 is connected to another exhaust pipe 15. A resonator 16 for preventing pulsation is connected to the exhaust pipe 15 in such a manner as to branch out from it. The upper end of the exhaust pipe 15 is open to the atmosphere. The portion of the exhaust pipe 15 that is open to the atmosphere extends into the inlet portion of a flue 17. An exhaust blower 18 is connected to the distal end of the flue 17.

An intake manifold is attached to a side of the engine 10 that is remote from the exhaust manifold 11. An intake pipe 19 is connected to the distal end of the intake manifold. The intake pipe 19 is further connected with a flowmeter 20 for measuring the flow rate of intake air E.

The exhaust gas measuring instrument in FIG. 1 has a mini-dilution tunnel 22. An inlet portion of the mini-dilution tunnel 22 is connected to an air introducing pipe 23. An air pump 24 is provided at the distal end of the air introducing pipe 23 to introduce dilution air. The distal end of the air introducing pipe 23, at which the air pump 24 is provided, is open opposite to an end of a dilution air supply pipe 25. The air introducing pipe 23 has a dilution air pressure regulating valve 26 placed in an intermediate position thereof.

A heat exchanger 27 is connected to the downstream side of the mini-dilution tunnel 22, and a blower 28 is connected to the downstream side of the heat exchanger 27. The blower 28 is a blower that rotates at a constant number of revolutions.

A bypass orifice 29 is installed in an erect portion of the exhaust pipe 15, which is connected to the downstream side of the muffler 14. One end of a sampling tube 30 is inserted into a portion of the exhaust pipe 15 below the bypass orifice 29. The sampling tube 30 extracts and introduces exhaust gas into the mini-dilution tunnel 22. A sample orifice 31 is installed in the sampling tube 30.

The bypass orifice 29 in the exhaust pipe 15 and the sample orifice 31 in the sampling tube 30 each act as a restrictor. The flow rate of exhaust gas flowing into each of the exhaust and sampling tubes 15 and 30 is distributed according to the air resistance ratio between the two orifices 29 and 31. Because the input pressures at the orifices 29 and 31 are almost the same, the exhaust gas flow rate split ratio R, that is, the ratio of the exhaust gas flow rate Qb in the exhaust pipe to the exhaust gas flow rate Qs in the sampling tube, i.e. Qb/Qs, is varied by controlling the output pressure.

A thin pipe 32' of small diameter having a sampling pump 32 for extracting a part of exhaust gas diluted in the mini-dilution tunnel 22 is inserted into the mini-dilution tunnel 22. A $NO_x$ meter 33 is connected downstream the sampling pump 32. The $NO_x$ meter 33 is further connected to a computer (CPU) 44 for control. In addition, another thin pipe 35' inserted into the mini-dilution tunnel 22 is connected with a particulate filter 34, a sampling pump 35, and a flowmeter 36.

A pretreatment device 37 is connected to a thin pipe 37' inserted into a portion of the exhaust pipe 15 at the outlet side of the muffler 14 and below the erect portion. A $NO_x$ meter 38 is connected to the downstream side of the pretreatment device 37. The $NO_x$ meter 38 is connected to the computer 44 for control.

A differential pressure gauge 39 is provided to detect a pressure difference between the two sides of the bypass orifice 29, which is provided in the erect portion of the exhaust pipe 15. The sampling tube 30, which extracts exhaust gas, is provided at a midway portion thereof with a differential pressure gauge 40 to detect a pressure difference between the two sides of the sample orifice 31. The detected outputs of these differential pressure gauges 39 and 40 are both input to the computer 44 for control.

Furthermore, the flowmeter 20 of the intake pipe 19 is connected to the computer 44 for control, together with a fuel gauge 41 for measuring the amount of fuel supplied to the engine 10. On the basis of the measured values by the flowmeter 20 and the fuel gauge 41, the computer 44 calculates the total amount of emission of exhaust gas, that is, the exhaust gas flow rate, when the engine 10 is at high temperatures. In addition, a tachometer of the blower 28 is connected to the computer 44. The computer 44 computationally obtains the flow rate in the mini-dilution tunnel 22 from the number of revolutions of the blower 28.

Figure 2:
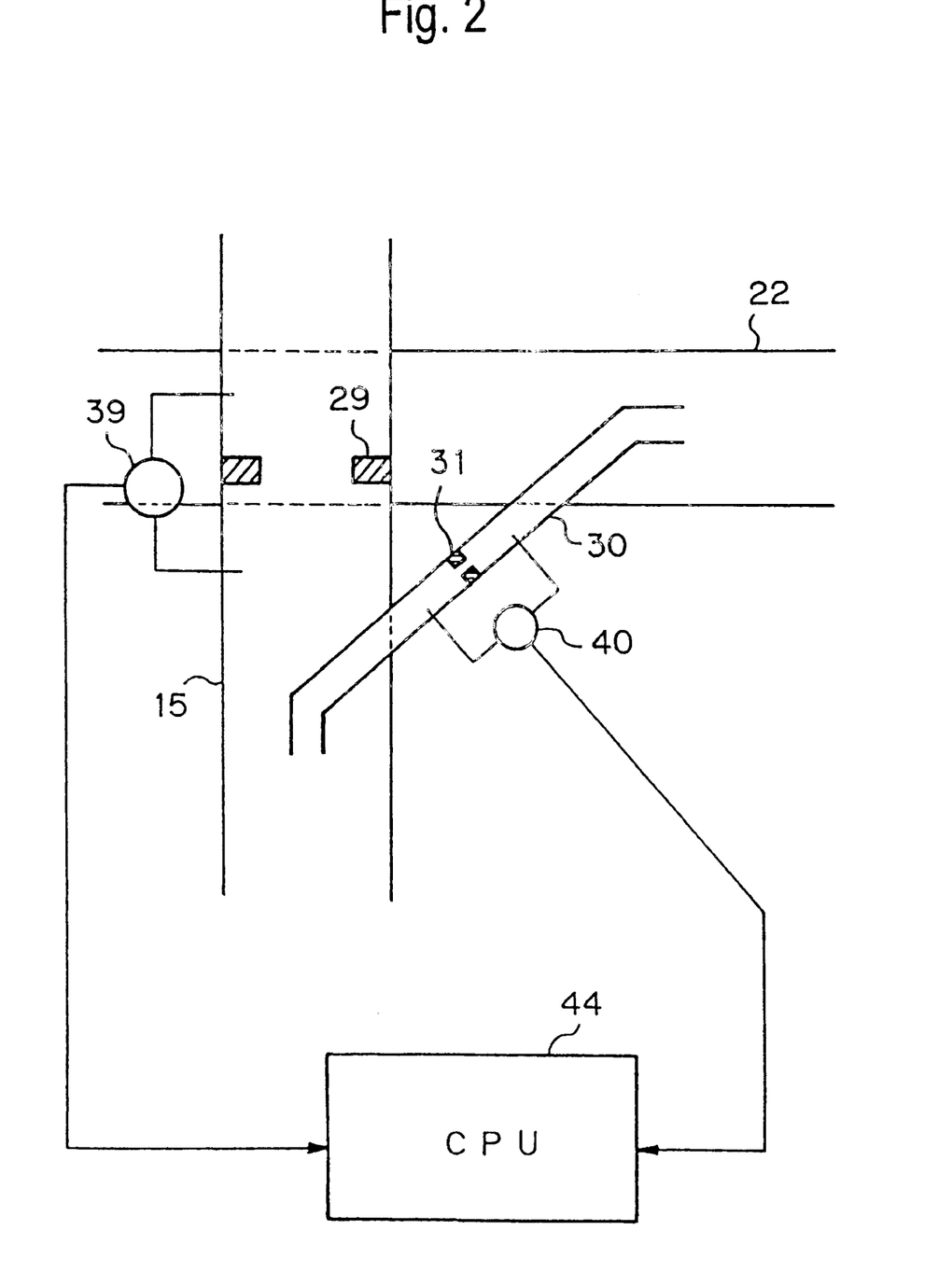
FIG. 2 is a fragmentary enlarged layout plan showing the way in which differential pressure gauges are installed.
Figure 3:
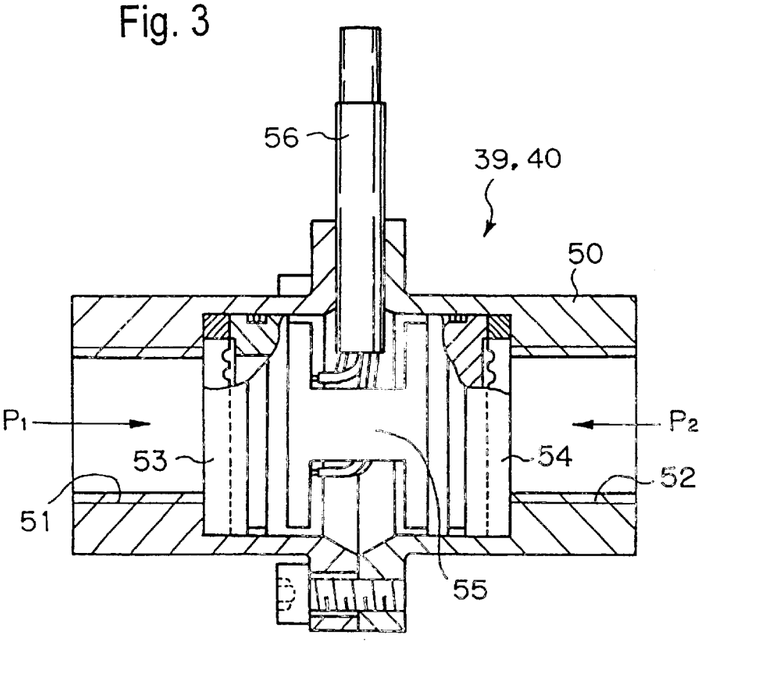
FIG. 3 is a fragmentary longitudinal sectional view showing the internal structure of a differential pressure gauge.

In this exhaust gas measuring instrument, a high response type differential pressure gauge is used as each of the differential pressure gauges 39 and 40 shown in FIG. 2. Such a differential pressure gauge has, as shown in FIG. 3, a cylindrical housing 50. The housing 50 has openings 51 and 52 at both sides thereof. Pressures P1 and P2 on the two sides of the orifice 29 (30) are applied to the two sides of the housing 50 through the openings 51 and 52. Pressure-receiving pistons 53 and 54 are placed inside the openings 51 and 52, respectively.

The pressure-receiving pistons 53 and 54 are each sealed at the outer peripheral portion thereof, and a transducer 55 is placed in the housing 50 in such a manner as to be sandwiched between the pressure-receiving pistons 53 and 54. The transducer 55 is a high response type transducer formed from a piezoelectric ceramic material to convert a pressure into an electric signal. The output of the transducer 55 is taken out through a cable 56.

Accordingly, when the pressures $P_1$ and $P_2$ on the two sides of the orifice 29 (31) are applied to the pressure-receiving pistons 53 and 54 through the openings 51 and 52, respectively, the transducer 55 detects a differential pressure between the pressures $P_1$ and $P_2$ on the two sides and transmits a detected signal to the computer 44 for control through the cable 56.

Figure 4:
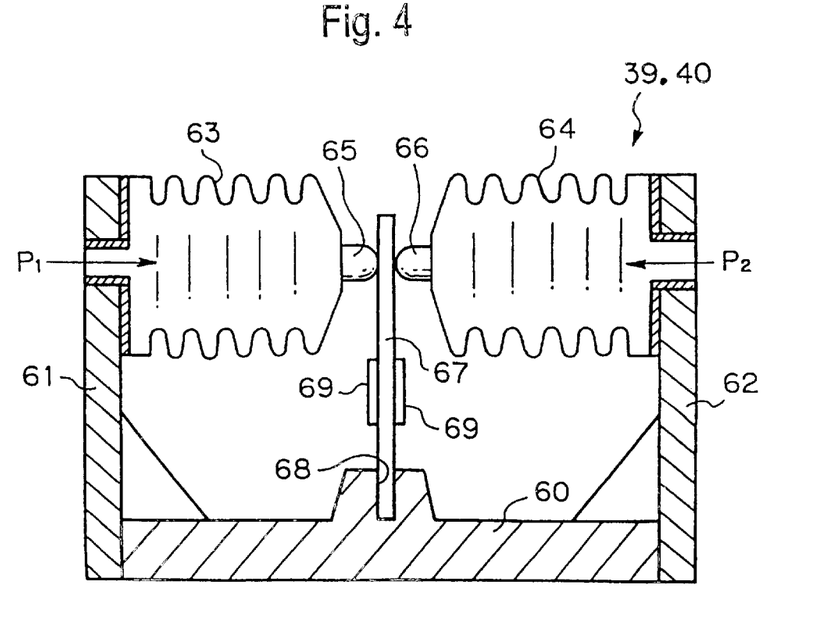
FIG. 4 is a fragmentary longitudinal sectional view showing the internal structure of another differential pressure gauge.

FIG. 4 shows another form of the differential pressure gauges 39 and 40. The differential pressure gauge has a base 60, and support plates 61 and 62 are erectly attached to both sides of the base 60. Bellows 63 and 64 are rigidly secured to the opposing side surfaces of the support plates 61 and 62. Pressure members 65 and 66 are attached to the respective distal ends of the bellows 63 and 64. The pressure members 65 and 66 are placed to press the opposite sides of a plate spring 67. The plate spring 67 has a lower end portion thereof secured by a sandwiching portion 68 of the base 60. A resistant-wire strain gauge 69 is attached to each side surface of the plate spring 67.

The pressures $P_1$ and $P_2$ on the two sides of the orifice 29 (31) are introduced into the bellows 63 and 64 of the differential pressure gauge 39 (40), and the bellows 63 and 64 extend or contract according to the introduced pressures. The pressure members 65 and 66 of the bellows 63 and 64 each press the plate spring 67, causing the plate spring 67 to be deflected. The deflection of the plate spring 67 is taken out through the resistant-wire strain gauges 69. The resistant-wire strain gauges 69 are connected into a bridge circuit, and the detected output is input to the computer 44 for control.

In the instrument of FIG. 1, exhaust gas generated by the operation of the engine 10 is discharged through the exhaust manifold 11 and the exhaust pipe 12. At this time, the exhaust pressure is regulated by the butterfly valve 13 for exhaust pressure regulation. Moreover, the exhaust pulsation is reduced by the muffler 14. A part of exhaust gas passing through the exhaust pipe 15 is extracted through the sampling tube 30 and introduced into the mini-dilution tunnel 22.

In the mini-dilution tunnel 22, the exhaust gas is diluted with air introduced through the air introducing pipe 23. Air for dilution is sent from the dilution air supply pipe 25 to the air introducing pipe 23 by the air pump 24.

The diluted exhaust gas is sampled by the sampling pump 32 and introduced to the $NO_x$ meter 33, where measurement of the amount of nitrogen oxides, that is, the $NO_x$ concentration Dt, is carried out. In addition, the diluted exhaust gas is sucked by the sampling pump 35 to pass through the particulate filter 34. At this time, the amount of particulate matter trapped by the filter 34 is measured.

The exhaust gas from the engine 10 before dilution is extracted directly from the exhaust pipe 15 through the thin pipe 37' at the outlet side of the muffler 14 and pretreated by the pretreatment device 37. Thereafter, the $NO_x$ concentration Db is measured by the $NO_x$ meter 38.

Next, an arrangement for controlling the amount of air sucked into the mini-dilution tunnel 22 through the air introducing pipe 23 will be described. The air pump 24, which is connected to the air introducing pipe 23, is driven to rotate by a motor 42. The number of revolutions of the motor 42 can be controlled by an inverter 43. The inverter 43 is controlled on the basis of a control command signal 43' from the computer 44.

To the computer 44, the exhaust gas flow rate Qt in the mini-dilution tunnel 22, the $NO_x$ concentration Dt in the mini-dilution tunnel 22, and the $NO_x$ concentration Db in the exhaust gas before dilution are input individually. The exhaust gas flow rate Qt in the mini-dilution tunnel 22 is measured by a method conformable to the method of measuring the flow rate in a dilution tunnel. The exhaust gas flow rate Qb in the exhaust pipe 15 is also measured as the sum of the intake air quantity and the fuel flow rate. The $NO_x$ concentration Dt in the mini-dilution tunnel 22 is measured with the $NO_x$ meter 33. The $NO_x$ concentration Db in the exhaust gas before dilution is measured with the $NO_x$ meter 38.

The exhaust gas concentration split ratio Rc of the exhaust gas in the mini-dilution tunnel 22 of the exhaust gas measuring instrument in FIG. 1 is calculated from the ratio of the whole quantity of $NO_x$ in the exhaust gas emitted from the engine 10 to the whole quantity of $NO_x$ in the diluted gas in the mini-dilution tunnel 22 on the assumption that $NO_x$ is a tracer gas. The concentration split ratio Rc is expressed by the following equation (1):

$$Rc=(Qb \cdot Db)/(Qt \cdot Dt) \qquad \text{Eq. (1)}$$

where Qb is the exhaust gas flow rate in the exhaust pipe; Db is the $NO_x$ concentration in the exhaust pipe; Qt is the diluted exhaust gas flow rate in the mini-dilution tunnel; and Dt is the $NO_x$ concentration in the mini-dilution tunnel.

On the other hand, the flow rate split ratio R in the mini-dilution tunnel is obtained from the following equation (2):

$$R=Qb/Qs \qquad \text{Eq. (2)}$$

where Qb is the exhaust gas flow rate in the exhaust pipe, and Qs is the exhaust gas flow rate in the sampling tube.

The computer 44 controls the number of revolutions of the motor 42 through the inverter 43 to thereby control the number of revolutions of the air pump 24 so that the flow rate split ratio R obtained by the computer 44 coincides with a desired value. By doing so, it becomes possible to feedback-control the flow rate split ratio R of the exhaust gas.

When the number of revolutions of the air pump 24 is changed, the pressure in the mini-dilution tunnel 22 changes, and this causes the flow rate split ratio to change. That is, if the number of revolutions of the pump 24 is increased to raise the pressure in the mini-dilution tunnel 22, it becomes difficult for the exhaust gas to enter the mini-dilution tunnel 22 through the sampling tube 30. Consequently, the flow rate split ratio R increases. If the number of revolutions of the pump 24 is reduced to lower the pressure in the mini-dilution tunnel 22, an increased amount of exhaust gas is introduced into the mini-dilution tunnel 22 through the sampling tube 30. As a result, the flow rate split ratio R reduces.

Thus, although the concentration split ratio Rc can be calculated by the computer 44 for control using Eq. (1), this method has the disadvantage that it requires several tens of seconds for the stabilization of the concentration of the tracer gas (in general, nitrogen oxides or carbonic acid gas), and therefore the response time is long. Accordingly, the method cannot be used during a transient operation of the engine.

In contrast, the calculation of the flow rate split ratio R based on Eq. (2) uses the differential pressure gauge 39 for the differential pressure between the two sides of the orifice 29 in the exhaust pipe 15 and the differential pressure gauge 40 for the differential pressure between the two sides of the orifice 31 in the sampling tube 30, and has the feature that the response is very fast. The use of Eq. (2) enables the flow rate split ratio R to be obtained with high accuracy even during a transient operation of the engine. However, the method using Eq. (2) has the disadvantage that it is readily affected by the use for a long period of time, temperature changes, etc. because of the use of orifices. Therefore, the flow rate split ratio R based on Eq. (2) is obtained, and the flow rate split ratio is calibrated by using the concentration split ratio Rc expressed by Eq. (1). By doing so, it is possible to obtain a flow rate split ratio with high accuracy during a transient operation of the engine.

In this embodiment, as shown in FIGS. 3 and 4, the high response type differential pressure gauge 39 is installed between the two sides of the orifice 29 in the exhaust pipe 15, and the high response type differential pressure gauge 40 is installed between the two sides of the orifice 31 in the sampling tube 30. The exhaust gas flow rate in the exhaust pipe 15 is obtained by measuring the differential pressure between the two sides of the orifice 29 with the differential pressure gauge 39 and input to the computer 44. The pressures on the two sides of the orifice 31 in the sampling tube 30 are detected with the differential pressure gauge 40, and the detected output is input to the computer 44. Thus, the exhaust gas flow rate Qb in the exhaust pipe 15 and the exhaust gas flow rate Qs in the sampling tube 30 are measured on the basis of the outputs of the differential pressure gauges 39 and 40. The flow rate split ratio R, which is the ratio between the two flow rates, is calculated by the computer 44 and output by a printer or a pen recorder.

Figure 5:
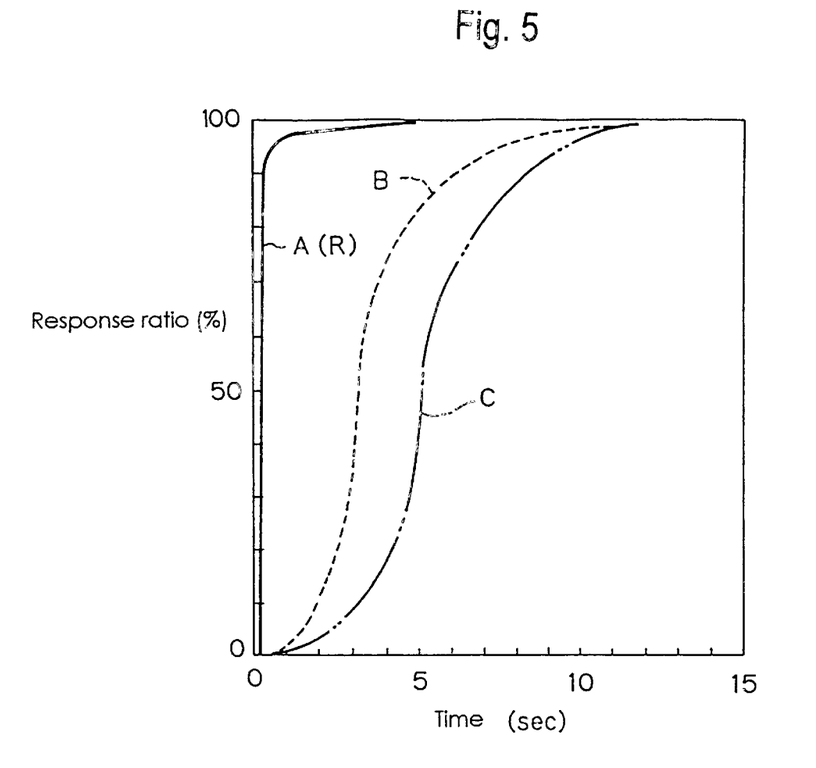
FIG. 5 is a graph showing the step response of differential pressure gauges.
Figure 6:
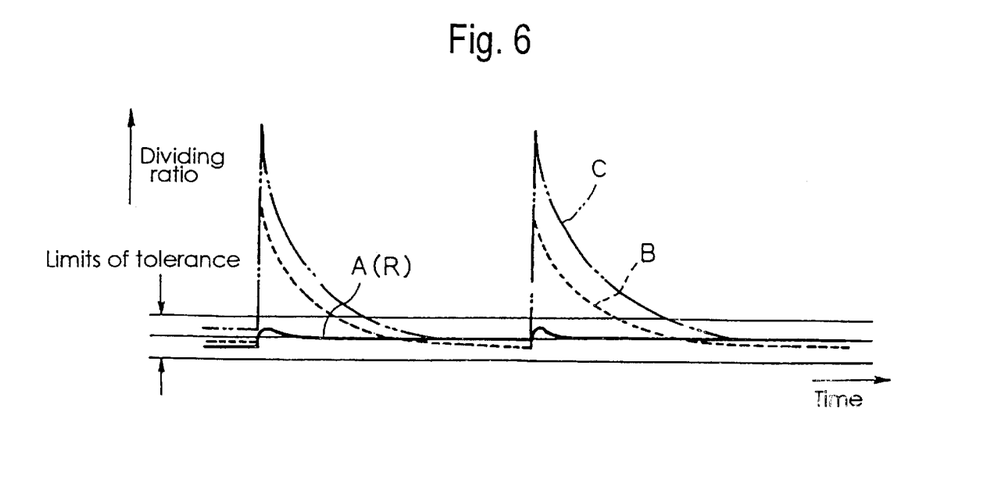
FIG. 6 is a graph showing the result of measurement of the split ratio by a measuring instrument using differential pressure gauges.

As shown in FIG. 5, the high response type differential pressure gauges 39 and 40 have characteristics represented by curve A. This shows that it is possible to obtain a response ratio more than ten times higher than curves B and C representing the characteristics of the conventional measuring methods. Thus, when the flow rate split ratio R is measured in the transient operation mode of the engine by using the high response type differential pressure gauges 39 and 40, the result of measurement falls within the limits of tolerance as shown by curve A in FIG. 6. Curves B and C in FIG. 6 show the results of measurement by the conventional measuring methods. Both the measurement results deviate from the limits of tolerance. The present invention enables measurement of the exhaust gas in the transient operation mode of the engine by a measuring instrument using the high response type differential pressure gauges 39 and 40 and the mini-dilution tunnel 22.

In the exhaust pipes 15 and 30, which are equipped with the differential pressure gauges 39 and 40, respectively, the orifices 29 and 31 may change with time, resulting in a change in the flow rate coefficient in each of the orifices 29 and 31. Therefore, to minimize the error in the measured value due to such a change, the flow rate split ratio R is multiplied by a calibration coefficient k to obtain a calibrated flow rate split ratio k·R. The calibration coefficient k is obtained in the form of the ratio of the concentration split ratio Rc to the flow rate split ratio R during a steady state operation of the engine, i.e. k=Rc/R. By obtaining the calibrated flow rate split ratio k·R in this way, it is possible to prevent the occurrence of an error due to aging in the measurement using the differential pressure gauges 39 and 40.

Thus, in the exhaust gas measuring instrument according to this embodiment, the mini-dilution tunnel is installed. In addition, the high response type differential pressure gauge 39 is installed between the two sides of the orifice 29, and the high response type differential pressure gauge 40 is installed between the two sides of the orifice 31, thereby obtaining a flow rate split ratio in the transient operation mode of the engine. Thus, the amount of emission of exhaust gas components can be measured. In other words, an exhaust gas measuring instrument using a mini-dilution tunnel for the steady state operation mode can be changed to an exhaust gas measuring instrument for the transient operation mode.

Advantageous Effects of the Invention

The principal effects and advantages of the present invention are as follows.

(1) The exhaust gas measuring instrument according to the present invention uses a mini-dilution tunnel. The mini-dilution tunnel is arranged to introduce thereinto a part of exhaust gas from the exhaust pipe of the engine and to dilute it with air. The mini-dilution tunnel merely dilutes a part of exhaust gas and can be reduced in size. Therefore, the overall size of the exhaust gas measuring instrument can be reduced.

(2) In the mini-dilution tunnel, the exhaust gas is placed in a state approximately similar to that in a case where it is released into the atmosphere, and in this state the amount of exhaust gas components are detected. Therefore, it is possible to obtain the necessary detection results relating to the engine performance evaluation and the emission regulations.

(3) The exhaust gas measuring instrument according to the present invention uses a high response differential pressure type bypassed gas flow meter and a high response differential pressure type extracted gas flow meter and is capable of obtaining a flow rate split ratio while satisfactorily following up changes in the operation conditions of the engine. Therefore, it is possible to perform exhaust gas measurement in the transient operation mode in addition to the steady state operation mode of the engine.

(4) The exhaust gas measuring instrument according to the present invention previously obtains a calibration coefficient and calibrates the flow rate split ratio, in which an error may be introduced owing to the time of use or by the effect of the environment, by multiplying the flow rate split ratio by the calibration coefficient. Therefore, an accurate exhaust gas measured value can be obtained independently of the passage of time of use or changes in the environment.

(5) In the exhaust gas measuring instrument according to the present invention, the calibration coefficient of the flow rate split ratio is obtained in the form of the ratio of the concentration split ratio to the flow rate split ratio during a steady state operation. Therefore, a constituent means provided in the exhaust gas measuring instrument can also serve as a means for obtaining the calibration coefficient, and no special means is needed.

What is claim is:

1. An exhaust gas measuring instrument comprising: a mini-dilution tunnel in which a part of exhaust gas in an exhaust pipe of an engine is introduced through a sampling tube and diluted with air; measuring means for measuring a specific component in the exhaust gas diluted in the mini-dilution tunnel; a high response differential pressure type extracted gas flow meter which measures an exhaust gas flow rate (Qs) in said sampling tube; a high response differential pressure type bypassed gas flow meter which includes an orifice-type sensor that measures an exhaust gas flow rate (Qb) in said exhaust pipe; and arithmetic means for obtaining a flow rate split ratio (R) by dividing the exhaust gas flow rate in the exhaust pipe, which is obtained by the high response differential pressure type bypassed gas flow meter, by the exhaust gas flow rate in the sampling tube, which is obtained by the high response differential pressure type extracted gas flow meter, and wherein the mini-dilution tunnel has an air pump (24) which supplies air into the mini-dilution tunnel, and a blower (28) for discharging diluted exhaust gas in the mini-dilution tunnel, said blower operating at a constant speed, and said air pump being operated at a controlled speed determined by the flow rate split ratio (R), said flow rate split ratio (R) being determined by a feed back control circuit, and said measuring means including a measuring device for measuring an amount of particulate in the diluted exhaust gas in said mini-dilution tunnel.

2. An exhaust gas measuring instrument according to claim 1, further comprising: means for obtaining a calibration coefficient (k) of the flow rate split ratio; and means for obtaining a calibrated flow rate split ratio (k·R) by multiplying the flow rate split ratio by said calibration coefficient in a transient operation mode of the of the engine, wherein the means for obtaining said calibration coefficient (k) includes measuring means for measuring the concentration ($D_b$) of a specific substance in the exhaust gas in the exhaust pipe during a steady state operation of the engine; means for obtaining a whole quantity ($Q_b \cdot D_b$) of the specific substance in the exhaust pipe by multiplying the exhaust gas flow rate ($Q_b$) in the exhaust pipe by the concentration of the specific substance in the exhaust gas in the exhaust pipe; means for measuring a diluted exhaust gas flow rate ($Q_t$) in the mini-dilution tunnel; measuring means for measuring the quantity ($D_t$) of the specific substance in the exhaust gas diluted in the mini-dilution tunnel; means for obtaining a whole quantity ($Q_t \cdot D_t$) of that specific substance in the mini-dilution tunnel by multiplying the diluted exhaust gas flow rate in the mini-dilution tunnel by the factor ($D_t$) of the specific substance in the exhaust gas diluted in the mini-dilution tunnel; and means for calculating a concentration split ratio (Rc) by dividing the whole quantity of the specific substance in the exhaust pipe by the whole quantity of the specific substance in the mini-dilution tunnel; and wherein said calibration coefficient (k) is obtained by dividing the concentration split ratio (Rc) by the flow rate split ratio (R).

3. An exhaust gas measuring instrument according to claim 2, specific substance is nitrogen oxides.

4. An exhaust gas measuring instrument according to claims 1 or 2, wherein the high response differential pressure type extracted gas flow meter has a sample orifice (31) installed in the sampling tube, and a differential pressure gauge (40) which detects a pressure difference between two sides of the sample orifice produced by the exhaust gas passing through the sample orifice whereby the differential pressure gauge detects a pressure difference at the sample orifice between one side and the other side thereof.

5. An exhaust gas measuring instrument according to claim 4. wherein the differential pressure gauge (40), which detects a pressure difference at the sample orifice, has first and second pressure-receiving pistons (53 and 54) and a transducer (55) placed between the two pressure-receiving pistons to convert a pressure into an electric signal, wherein a pressure on one side of the sample orifice and a pressure on the other side of the sample orifice are applied to the first and second pressure-receiving pistons, respectively, whereby a pressure difference produced at the sample orifice is converted into an electric signal.

6. An exhaust gas measuring instrument according to claim 4. wherein the differential pressure gauge (40), which detects a pressure difference at the sample orifice, has first and second bellows (63 and 64) and a resistant-wire strain gauge (69) which converts deformation of a plate spring (67), which is placed between the two bellows, into an electric signal, wherein a pressure on one side of the sample orifice and a pressure on the other side of the sample orifice are applied to the first and second bellows, respectively, whereby a pressure difference produced at the sample orifice is converted into an electric signal.

7. An exhaust gas measuring instrument according to claim 1 or 2, wherein the high response differential pressure type bypassed gas flow meter has a bypass orifice (29) installed in the exhaust pipe, and a differential pressure gauge (39) which detects a pressure difference between two sides of the bypass orifice produced by the exhaust gas passing through the bypass orifice.

8. An exhaust gas measuring instrument according to claim 7, wherein the differential pressure gauge (39), which detects a pressure difference at the bypass orifice, has first and second pressure-receiving pistons and a transducer placed between the two pressure-receiving pistons to convert a pressure into an electric signal, wherein a pressure on one side of the bypass orifice and a pressure on the other side of the bypass orifice are applied to the first and second pressure-receiving pistons, respectively, whereby a pressure difference at the bypass orifice is converted into an electric signal.

9. An exhaust gas measuring instrument according to claim 7, wherein the differential pressure gauge (39), which detects a pressure difference at the bypass orifice, has first and second bellows (63 and 64) and a resistant-wire strain gauge (69) which converts deformation of a plate spring (67), which is placed between the two bellows, into an electric signal, wherein a pressure on one side of the bypass orifice and a pressure on the other side of the bypass orifice are applied to the first and second bellows, respectively, whereby a pressure difference at the bypass orifice is converted into an electric signal.

10. An exhaust gas measuring instrument according to claims 1 or 2, wherein the high response differential pressure type bypassed gas flow meter measures the exhaust gas flow rate (Qb) in the exhaust pipe as a sum of an intake air quantity and a fuel flow rate.

11. An exhaust gas measuring instrument according to claims 1 or 2, wherein the high response differential pressure type bypassed gas flow meter, which measures the exhaust gas flow rate in said exhaust pipe, measures a flow rate of exhaust gas remaining after a part of exhaust gas has been extracted through said sampling tube.

* * * * *

UNITED STATES PATENT AND TRADEMARK OFFICE
CERTIFICATE OF CORRECTION

PATENT NO.     : 6,460,400 B1
DATED          : October 8, 2002
INVENTOR(S)    : Jun Ichikawa

It is certified that error appears in the above-identified patent and that said Letters Patent is hereby corrected as shown below:

<u>Title page,</u>
Item [75], the Inventor's information should read -- Jun Ichikawa, Tokyo, (JP) --.

<u>Column 10,</u>
Line 29, -- wherein said -- should be inserted after "2,".

Signed and Sealed this

Eighteenth Day of March, 2003

JAMES E. ROGAN
*Director of the United States Patent and Trademark Office*